United States Patent
Gershteyn

(10) Patent No.: US 7,472,700 B2
(45) Date of Patent: Jan. 6, 2009

(54) ADAPTOR FOR RELEASABLY MOUNTING A VAPORIZER ON AN ANESTHESIA MACHINE

(75) Inventor: Jacob Gershteyn, Newtown, PA (US)

(73) Assignee: Drager Medical AG & Co. KG, Lubeck (DE)

( * ) Notice: Subject to any disclaimer, the term of this patent is extended or adjusted under 35 U.S.C. 154(b) by 926 days.

(21) Appl. No.: 10/918,624

(22) Filed: Aug. 12, 2004

(65) Prior Publication Data

US 2006/0032502 A1     Feb. 16, 2006

(51) Int. Cl.
- A61M 16/20  (2006.01)
- A61M 16/18  (2006.01)
- F16K 35/14  (2006.01)
- G05G 11/00  (2006.01)

(52) U.S. Cl. ............... 128/203.12; 128/203.14; 128/202.22; 128/205.24; 74/483 K; 74/483 R; 74/473.25; 137/625; 137/637.1; 251/111; 251/149.9

(58) Field of Classification Search ............ 128/200.14, 128/200.19, 202.22, 203.12, 203.13, 203.14, 128/103.19, 203.24, 205.27, 206.16, 206.17, 128/206.29; 74/483 K, 483 R, 473.25, 493.26; 137/637.1, 635; 261/DIG. 65; 251/149.9, 251/111

See application file for complete search history.

(56) References Cited

U.S. PATENT DOCUMENTS

| | | | | |
|---|---|---|---|---|
| 3,389,618 A | * | 6/1968 | McDermott | 475/168 |
| 3,831,599 A | * | 8/1974 | Needham | 128/203.12 |
| 4,058,120 A | * | 11/1977 | Caparrelli et al. | 128/203.12 |
| 4,246,115 A | * | 1/1981 | Swank | 210/167.04 |
| 4,307,718 A | * | 12/1981 | Schreiber | 128/200.19 |
| 4,308,865 A | * | 1/1982 | Hay | 128/200.14 |
| 4,346,701 A | * | 8/1982 | Richards | 128/200.14 |
| 4,351,327 A | * | 9/1982 | Rinne et al. | 128/200.14 |
| 4,434,790 A | * | 3/1984 | Olesen | 128/200.14 |
| 4,463,754 A | * | 8/1984 | McDonald | 128/200.14 |
| 4,759,358 A | | 7/1988 | Gregory | |
| 4,932,398 A | * | 6/1990 | Lancaster et al. | 128/200.14 |
| 6,962,153 B2 | * | 11/2005 | Gershteyn | 128/203.12 |

* cited by examiner

*Primary Examiner*—Justine R Yu
*Assistant Examiner*—Clinton Ostrup
(74) *Attorney, Agent, or Firm*—Caesar, Rivise, Bernstein, Cohen & Pokotilow, Ltd.

(57) ABSTRACT

An adapter for use on an anesthesia machine having of three or more vaporizer units removably mounted thereon by an interlock/exclusion system. The interlock/exclusion system includes plural vertically oriented pins that are coupled together and are operative to move upward to prevent opening of any vaporizer units if one is open. One of the vaporizer units includes a horizontally oriented pin which moves outward when that unit is opened. The adaptor is arranged to mount that vaporizer on the machine and to couple the horizontally oriented pin to an associated vertically oriented pin of the interlock/exclusion system.

14 Claims, 7 Drawing Sheets

ADAPTOR FOR RELEASABLY MOUNTING A VAPORIZER ON AN ANESTHESIA MACHINE

CROSS REFERENCE TO RELATED APPLICATIONS

"Not Applicable"

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

SPECIFICATION

BACKGROUND OF THE INVENTION

1. Field of Invention

This invention relates generally to anesthesia machines, and more particularly to devices for mounting vaporizers on anesthesia machines equipped interlocks or exclusion systems for precluding operation of any vaporizer if another is in use.

2. Description of Related Art

It is common practice for an anaesthesia apparatus to have mounted on it two or more separate vaporizers, each arranged for delivering a different volatile anaesthetic so that the same basic anaesthesia apparatus can be used during a series of surgical operations to meet the needs of different patients.

In U.S. Pat. No. 4,759,358 (Gregory) there is disclosed an interlock system for use with two or more gas flow units (vaporizers) when mounted in a removable plug-in fashion on the back bar of an anaesthesia machine. Each gas flow unit includes a rotary cap, which when moved from an off to an on or operative position admits to the unit a gas from a supply provided by the apparatus. The interlock system includes at least one pin associated with each gas flow unit which, when the rotary cap is moved towards its operative position, extends outwardly from the unit to engage and move a spacer mounted for sliding movement on the apparatus between adjacent units towards a similar adjacent unit to thereby prevent the rotary cap of the similar adjacent unit from being moved towards its operative position.

Datex-Ohmeda, Inc. of Madison, Wis., presently commercializes vaporizers for use in anesthesia machines constructed in accordance with the teachings of U.S. Pat. No. 4,759,358. Those vaporizers are a series sold under the designation "TEC" vaporizers.

In my co-pending U.S. patent application Ser. No. 10/681,787, filed on Oct. 7, 2003, entitled Interlock/Exclusion Systems for Multiple Vaporizer Anesthesia Machines, now U.S. Pat. No. 6,962,153, assigned to Draeger Medical, Inc. of Telford, Pa., the same assignee as this invention, and whose disclosure is incorporated by reference herein there is disclosed an interlock/exclusion system adapted for use with plural vaporizers on an anesthesia machine.

The machine is configured for use with at least three, removable vaporizers. Each vaporizer is identical in construction, except for the particular anesthesia it is arranged to provide to the anesthesia machine and is arranged to be releasably mounted on the anesthesia machine in a removable plug-in fashion. In accordance with one preferred exemplary embodiment of the invention in that application each of the vaporizers is a conventional device, such as that sold under the trademark VAPOR 2000 by Draeger Medical, Inc. Each vaporizer unit includes its own respective built-in adaptor to enable it to be mounted on the anesthesia machine in a removable, plug-in fashion. An interlock/exclusion system of my aforementioned patent application is designated under the trademark Autoexclusion 3 Vapor mount bar and is included on the FABIUS GS anesthesia machine of Draeger Medical, Inc.

Owing to the particular construction of the interlock/exclusion system of my aforementioned patent application, a purchaser/user of the Fabius GS3 anesthesia machine or some other machine making use of an interlock/exclusion system of my aforementioned patent application can only make use of vaporizers constructed like those disclosed in that application, e.g., VAPOR 2000 units.

A need thus exists for an adaptor or other device to enable a vaporizer like that of U.S. Pat. No. 4,759,358 to be used with an anesthesia machine constructed in accordance with the teachings of my aforementioned patent application.

All references cited herein are incorporated herein by reference in their entireties.

BRIEF SUMMARY OF THE INVENTION

An adaptor for use with an anesthesia machine arranged to have a first, second and third gas flow units, e.g., vaporizers, removably mounted thereon by an interlock/exclusion system. Each of the gas flow units is arranged to be opened to enable the machine to provide a gas to a patient. The interlock/exclusion system comprises vertically oriented pin assemblies associated with respective ones of the gas flow units. The vertically oriented pin assemblies are coupled together, whereupon when one of the gas flow units is opened a vertically oriented pin of the assembly associated with it is moved downward and the vertically oriented pins of the assemblies associated with other gas flow units are moved upward to preclude the opening of those gas flow units.

The adaptor is arranged to be mounted on the interlock/exclusion system and coupled to one of the vertically oriented pins for releasably mounting one of said gas flow units on the machine. That gas flow unit has a horizontally oriented pin arranged to move horizontally outward therefrom when the gas flow unit is opened. The adaptor is constructed to couple the outward motion of the horizontally oriented pin to the said one vertically oriented pin of the interlock/exclusion system to move the said one pin downward, whereupon the interlock/exclusion system operates to cause the other vertically oriented pins to extend upward and thereby prevent the opening of the other two vaporizers.

In accordance with one preferred aspect of this invention the adaptor comprises a first movable, e.g., pivotable, member and a second movable member. The first member is pivotable about a horizontal axis and has an upper end located adjacent the horizontally oriented pin of the gas flow unit. The second movable member is coupled to the first movable member and has a downward sloping cam face adapted to engage the said one pin to push the said one pin downward when the gas flow unit is opened.

In accordance with another preferred aspect of this invention the adaptor additionally comprises at least one rod. The second movable member is pivotable about a vertical axis and has a first end portion at which the cam surface is located and a second end portion. The first movable member has a lower end. The at least one rod is coupled between the lower end of the first movable member and the second end of second movable member.

In accordance with another preferred aspect of this invention the adaptor includes a spring to bias the second end of the second movable member into engagement with the at least one rod.

In accordance with another preferred aspect of this invention the adaptor is arranged to be releasably mounted on the interlock/exclusion system by a locking assembly.

In accordance with another preferred aspect of this invention the adaptor includes another locking assembly for releasably locking the gas flow unit on the adaptor.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1:
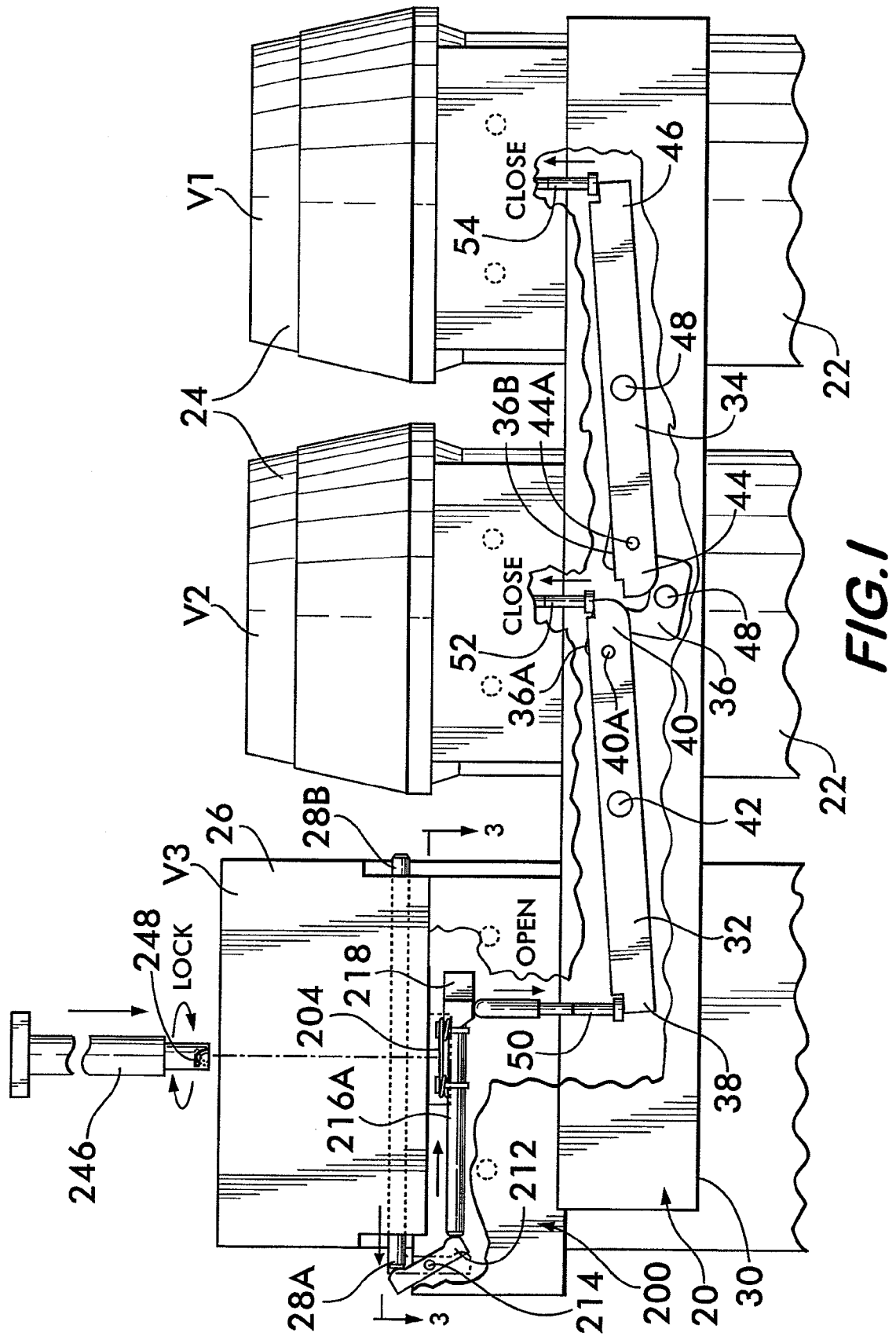
FIG. 1 is an elevation view, partially broken away, of portion of an anesthesia machine including three removable vaporizer units mounted on an interlock/exclusion system constructed in accordance with the teachings of my aforementioned patent application, with one of the vaporizers being mounted on the exclusion system by an adaptor constructed in accordance with one exemplary embodiment of the subject invention and being shown in its open position, whereupon the interlock/exclusion system prevents the other two vaporizers from being opened.

Referring now to the various figures of the drawing wherein like reference characters refer to like parts, there is shown generally at 20 an interlock/exclusion system constructed in accordance with the teachings of my aforementioned patent application and mounted on an anesthesia machine (not shown). In accordance with one preferred embodiment of this invention the anesthesia machine with the interlock/exclusion system 20 is constructed like the aforementioned Autoexclusion 3 vapor mount bar of the FABIUS GS machine. That machine is configured for use with at least three, removable vaporizers V1, V2 and V3. The vaporizers V1 and V2 are identical in construction, except for the particular anesthesia they are arranged to provide to the machine and each vaporizer is arranged to be releasably mounted on the machine in a plug-in fashion via its associated built-in adaptor. The vaporizers V1 and V2 are conventional devices, such as the aforementioned VAPOR 2000 vaporizers. The other vaporizer V3 is of a different construction, i.e., is constructed in accordance with the teaching of U.S. Pat. No. 4,759,358. The vaporizer V3 is also arranged to be mounted on the machine in a removable plug-in fashion via the interlock/exclusion system 20. In order to effect such a mounting and to ensure that the vaporizer V3 cooperates with the interlock/exclusion system 20 an adaptor 200 is provided. The adaptor 200 constitutes the subject matter of this invention.

It should also be pointed out at this juncture that the adaptor of this invention is not limited to use on an interlock/exclusion system equipped anesthesia machine. Thus, it and can be used on any type of gas administration apparatus making use of three or more removable gas flow units and an interlock exclusion system constructed in accordance with the teachings of my aforementioned patent application.

As best seen in FIG. 1 each of the vaporizers V1 and V2 comprises a canister 22 containing the anesthesia vapor to be dispensed and the means for metering the same into a gas line (not shown) of the anesthesia machine. The concentration of the anesthesia vapor provided by each of the vaporizers V1 and V2 is determined by the setting of its vapor concentration adjusting dial 24. That dial basically comprises a generally disk-shaped member having a circular, outer surface that is sloped downward and is ribbed to provide a manual gripping. The vaporizer's canister 22 includes a pointer (not shown) to indicate the particular vapor concentration setting as established by the vaporizer's dial 24. To that end indicia (not shown) indicative of the vapor concentration amount are provided along the periphery of the dial 24. In particular, the rotation of the vaporizer dial in the counter-clockwise direction opens the vaporizer to introduce vaporized gas into a patient breathing circuit (not shown) of the machine, with the concentration level established by the setting of the dial being displayed or indicated by the particular indicium that is disposed opposite to the pointer. Each vaporizer is also arranged to be set to a "transport position" wherein the vaporizer is closed, i.e., no anesthesia will be permitted to exit the vaporizer. Each vaporizer V1 and V2 also includes a ring (not shown) located under its dial. The undersurface of each ring includes a recess that has a cam surface (ramp) trailing from it to the planar undersurface of the ring. The vaporizer's dial 24 engages the ring, so that rotation of the dial causes concomitant rotation of the ring. Each vaporizer V1 and V2 includes its own built-in adaptor to mount it on the interlock/inclusion system 20.

The vaporizer V3 includes a canister 22 containing the anesthesia vapor to be dispensed and the means for metering the same into a gas line (not shown) of the anesthesia machine. The concentration of the anesthesia vapor provided by the vaporizers V3 is determined by the setting of a vapor concentration adjusting dial (not shown) on the body. The vapor concentration dial is provided for controlling the admission to the vaporizer gas into the patient breathing circuit. Any rotational movement of a concentration dial from its off position is transmitted via cams, cranks, spring loaded platforms and pins (not shown) to two pins 28A and 28B which are caused to extend outwardly from the body of the vaporizer V3. When used with an anesthesia machine like that constructed in accordance with the teachings of U.S. Pat. No. 4,759,358 one of the pins 28A or 28B is arranged to cooperate with a spacer that is mounted for sliding movement on a back bar of the anesthesia machine. The spacer is generally channel-shaped split member mounted for sliding movement on the machine and together with the pins forms the interlock of the anesthesia machine of that patent.

As will be described in detail later the adaptor 200 of this invention is arranged to be mounted on the interlock/exclusion system 20 to enable the vaporizer V3 to be mounted on the machine in a removable plug-in fashion and with the interlock/exclusion system 20 being fully operative and functional.

As described in detail in my aforementioned patent application the interlock/exclusion system 20 is arranged to enable any vaporizer unit V1, V2 or V3 to be opened to a desired concentration level, provided that no other vaporizer unit is already open, and to preclude any vaporizer unit from being opened if one vaporizer unit is already open. Moreover, since the vaporizer units are arranged to be removably mounted on the anesthesia machine, the interlock/exclusion system is operative to prevent the opening of any vaporizer unit if one is already open, irrespective of whether or not all of the vaporizer units are mounted on the machine. Thus, with the exemplary embodiment of the interlock/exclusion system 20 making use of the adaptor 200, any one of the three vaporizer units V1, V2 or V3 can be removed from the machine and the interlock/exclusion system will still be operative to prevent the opening of one of the two remaining vaporizer units if the other of those two vaporizers is open.

It should be pointed out at this juncture that the interlock/exclusion system 20 can be configured to accommodate any number of removable vaporizer units in excess of two. Moreover, such interlock/exclusion systems are also operative to prevent opening of any vaporizer unit if one vaporizer unit is already open and irrespective of how many vaporizer units are mounted on the machine at the time.

Before discussing the details of the subject adaptor 100, a brief description of the interlock/exclusion system 20 is in order. To that end, it basically comprises a vaporizer bracket 30 for mounting the vaporizer units V1, V2 and V3 on the machine via their respective built-in adaptors. The interlock exclusion system includes a pair of elongated pivotable bars 32 and 34, a pivotable coupling 36, and plural pins and associated components (to be described later).

The pivotable bar 32 is an elongated, linear member having a first end 38 and a second end 40. The bar is pivotably mounted on the bracket 30 by a pivot pin 42 extending through the middle of it. Thus, the bar 32 can be pivoted either clockwise or counterclockwise about the pivot axis established by the pivot pin 42. The second end 40 of the bar 32 is bifurcated to form a yoke-like structure having a pair of spaced arms (not shown). The space between the arms is arranged to accommodate a portion of the pivotable coupling 36. The pivotable bar 34 is an elongated member, constructed similar to bar 32 but oriented as a mirror image thereof. Thus, the bar 34 has a first end 44 and a second end 46, with the first end 44 being bifurcated to form a yoke like structure having a pair of spaced arms. The space between those arms is arranged to accommodate another portion of the pivotable coupling 36. The pivotable bar 34 is pivotably mounted on the bracket 30 by a pivot pin 48 extending through the middle of the bar. The bar 34 can be pivoted either clockwise or counterclockwise about the pivot axis established by the pivot pin 44.

The pivotable coupling 36 basically comprises a plate-like, generally T-shaped member having a first end portion in the form of an outwardly extending hook 36A and a second end portion in the form of an outwardly extending hook 36B disposed opposite to and aligned with the first hook 36A. The coupling 36 is located between the second end 40 of the first bar 32 and the first end 44 of the second bar 34 to couple those bars together. In particular, the hook 36A of the coupling 36 is disposed in the space between the yoke arms at the second end 40 of the first pivotable bar 32, while the other hook 36B is disposed in the space between the yoke arms at the first end 44 of the second pivotable bar 34. A pin 40A extends through the arms of the yoke at the second end 40 of the first pivotable bar 32, with the hook 36A of the coupling 36 disposed over and engaging that pin. In a similar manner a pin 44A extends through the arms of the yoke at the first end 44 of the second bar 34, with the hook 36B of the coupling 36 disposed over and engaging that pin.

The coupling 36 is mounted on the bracket 30 by a pivot pin 48 extending through the middle of the coupling. Thus, the coupling can be pivoted either clockwise or counterclockwise about the pivot axis established by the pivot pin 48.

The exemplary embodiment of interlock/exclusion system 20 shown includes three assemblies 50, 52 and 54 including follower pins. Each of these assemblies comprise a plurality of components (e.g., pins, levers, springs, etc.) which are fully described in my aforementioned copending patent application. In the interest of drawing simplicity each assembly is graphically represented in the drawings of this application by a vertically oriented, follower pin that is arranged to be reciprocated upward and downward. The follower pin assemblies 54 and 52 are coupled to respective ones of the vaporizer units V1 and V2 via the built-in adaptors for those vaporizer units, while the follower pin assembly 50 is coupled via the adaptor 200 of this invention for the vaporizer unit V3.

The follower pin assembly 50 cooperates with a mechanism (to be described later) in the adaptor 200 to couple the vaporizer unit V3 to the pivoting bar 32 of the interlock/exclusion system 20. The follower pin assembly 52 is associated with the vaporizer unit V2 and is coupled the pivotable bars 32 and 34 of the interlock/exclusion system 20. The upper end of the follower pin assembly 52 is arranged engage the undersurface of the ring of the vaporizer unit V2. In particular, the upper end of the follower pin assembly 52 is arranged to be disposed within the recess in the ring of the vaporizer unit V2 when that vaporizer unit in closed and to ride down the cam surface onto the underside surface of the ring when that vaporizer unit is opened. The follower pin assembly 52 is mounted within the built-in adaptor making up a portion of the vaporizer unit V2 and is coupled to the second end 40 of the first pivotable bar 32 and to the first end 44 of the second pivotable bar 34.

The follower pin assembly 54 is associated with the vaporizer unit V1 and is associated with the second pivotable bar 34. The upper end of the follower pin assembly 54 is arranged engage the undersurface of the ring of the vaporizer unit V1. In particular, the upper end of the follower pin 54 is arranged to be disposed within the recess in the ring of the vaporizer unit V1 when that vaporizer unit is closed and to ride down the cam surface onto the underside surface of the ring when that vaporizer unit is opened. The follower pin assembly 54 is mounted within the built-in adaptor making up a portion of the vaporizer unit V1 and is coupled to the second end 46 of the second pivotable bar 34.

The upper end of each follower pin assembly 50, 52 and 52 includes a cylindrical member having a domed upper surface. The lower end of each follower pin assembly includes a cylindrical lower end terminating in a generally planar lower surface.

As noted above, a vaporizer unit constructed in accordance with the teaching of U.S. Pat. No. 4,759,358, such as vaporizer unit V3, is arranged when opened to have its pins 28A and 28B extend outward horizontally from a retracted position to an extended position. Either of these pins is arranged when extended to engage a sliding member when used with an anesthesia machine like that described in that patent to prevent the opening of any other similarly constructed vaporizer units on the anesthesia machine (assuming any such units are mounted on the machine). The particular pin 28A or 28B that engages the sliding member of the interlock of that patent is a function of the position that the vaporizer unit is located on the anesthesia machine.

With the vaporizer unit V3 mounted on the interlock/exclusion system 20 at the leftmost position shown in FIG. 1, the pin 28A serves to couple the vaporizer unit V3 to the interlock/exclusion system 20 via the adaptor 200.

Before describing the details of the construction and operation of the adaptor 200 a brief description of the operation of the interlock/exclusion system 20 is in order. To that end, assuming that all of the vaporizer units V1, V2 and V3 are closed, the operation of the interlock/exclusion system 20 when the vaporizer unit V3 is opened will now be discussed. When the vapor concentration dial of the vaporizer unit V3 is rotated to the on position a mechanism within the vaporizer causes the pin 28A to be extended outward, like shown in FIG. 1. This action causes a component (to be described later) of the adaptor 200 to push downward on the domed top end surface of the follower pin assembly 50. This action causes the bottom surface lower end of the follower pin assembly 50 to push downward on the first end 38 of the pivot bar 32, whereupon the pivot bar 32 pivots in a counter-clockwise direction. The pivoting of the pivot bar 32 in this direction causes its second end 40 to pivot upward, whereupon the top surface of that end engages the bottom end of the follower pin assembly 52 to push the upper end of that assembly upward and thereby hold it within the recess at the underside of the dial of the vaporizer unit V2. Accordingly, the dial 24 of that vaporizer unit cannot be rotated to open that vaporizer unit.

The pivoting of the first pivot bar 32 as described above when the vaporizer unit V3 is opened also causes the second pivot bar 34 to be pivoted counter-clockwise with the first pivot bar. In particular, the upward movement of the second end 40 of the first pivot bar 32 causes its associated pin 40A to push upward on the hook 36A of the coupling 36, thereby pivoting the coupling in the clockwise direction. This action causes the hook 36B on the opposite side of the coupling to press downward on the pin 44A at the first end 44 of the second pivot bar 34. Accordingly, the second pivot bar 34 pivots in the counter-clockwise direction. This action causes the top surface of the second end 46 of the second pivot bar 34 to engage the bottom end surface of the follower pin assembly 54 to push the upper end of that assembly upward and thereby hold it within the recess at the underside of the dial of the vaporizer unit V1. Accordingly, the dial 24 of that vaporizer unit cannot be rotated to open that vaporizer unit.

As will be appreciated by those skilled in the art, the interlock/exclusion system 20 will operate as described to prevent the opening of the middle vaporizer V2, even if the rightmost vaporizer V1 has been removed from the anesthesia machine. So too, the system 20 will prevent the opening of the rightmost vaporizer unit V1 even if the middle vaporizer V2 has been removed from the anesthesia machine.

Assuming that the middle vaporizer unit V2 is the unit desired to be opened, it is necessary to close any vaporizer unit that had previously been opened. Thus, assuming that the leftmost vaporizer unit V3 had been opened (as in the previous example), it will be necessary to close it before opening the middle vaporizer unit V2. To that end the dial of the vaporizer unit V1 is rotated back to the closed position, thereby retracting the pin 28A from its extended position (shown in FIG. 1) to its fully retracted position (not shown). This action causes the mechanism in the adaptor 200 to enable the upper portion of the follower pin assembly 50 to move upward, whereupon the lower portion of that assembly also moves upward. At this time all of the vaporizer units will be closed. Thus, one can then rotate the dial 24 of the second (middle) vaporizer unit V2 to open it.

The rotation of the dial 24 of the middle vaporizer unit 22B, causes the upper surface portion of the follower pin assembly 52 to begin to ride on the cam surface of its associated ring to push it downward. The downward force applied to the second follower pin assembly as it rides down the cam surface and onto the undersurface of the ring of that vaporizer causes the bottom surface portion of the follower pin assembly 52 to engage the top surface of the second end 40 of the first pivot bar 32 and the first end 44 of the second pivot bar 34.

The downward force on the second end of the first pivot bar 32 pivots it in a clockwise direction. The pivoting of the first pivot bar 32 in this direction causes the top surface of its first end 38 to pivot upward, whereupon it engages bottom surface portion of the follower pin assembly 50 to push it upward and thereby cause the mechanism within the adaptor 20 to hold the pin 28A of the vaporizer unit V3 in its retracted position. This action prevents the vaporizer unit V3 from being opened.

The downward force on the first end of the second pivot bar 34 pivots it in a counter-clockwise direction to cause the top surface of its second end 34 to pivot upward, whereupon the upward force is coupled through the follower pin assembly 54 to cause the surface portion at the top end thereof to be held within the recess of the vaporizer unit V1, so that its dial cannot be rotated to open it.

Further turning of the dial 24 of the middle vaporizer unit V2 establishes the desired rate of flow of anesthesia therefrom, while the interlock/exclusion system 20 prevents the other two vaporizer units V3 and V1 from being opened.

Operation of the interlock/exclusion system when the third (rightmost) vaporizer unit V1 is opened is similar to the operation of the system when the first (leftmost) vaporizer unit V3 is opened and will not be described in detail in the interest of brevity.

Figure 3:
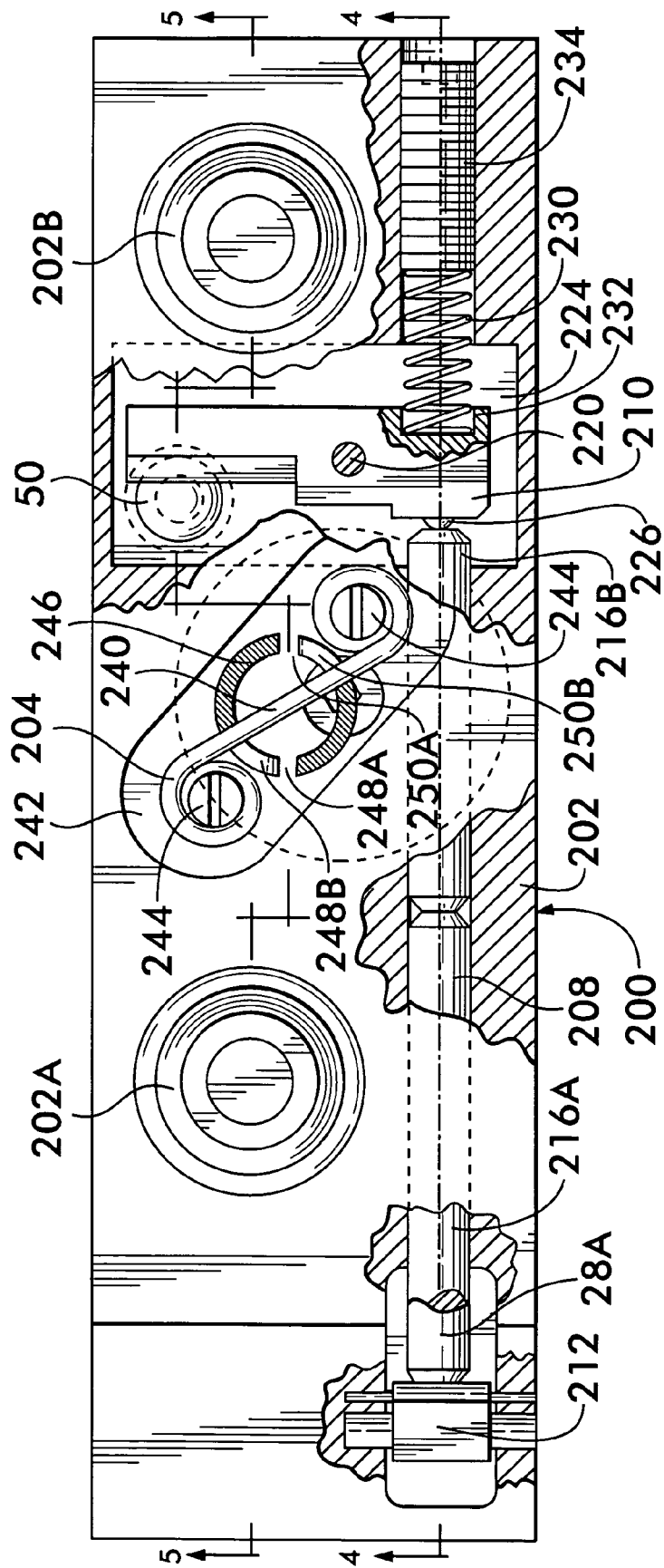
FIG. 3 is an enlarged sectional view, partially broken away, taken along line 3-3 of FIG. 1.
Figure 4:
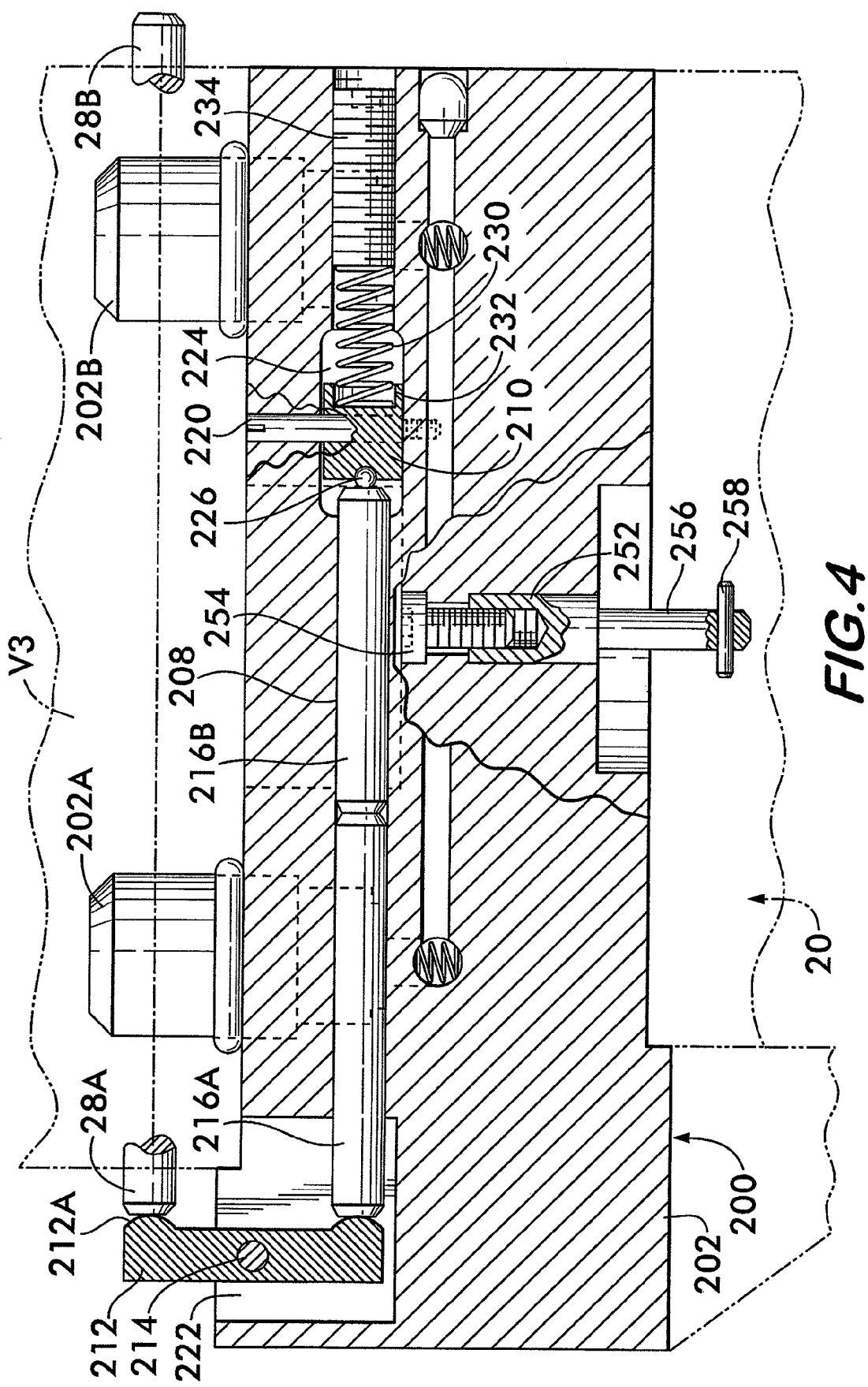
FIG. 4 is a sectional view taken along line 4-4 of FIG. 3.
Figure 5:
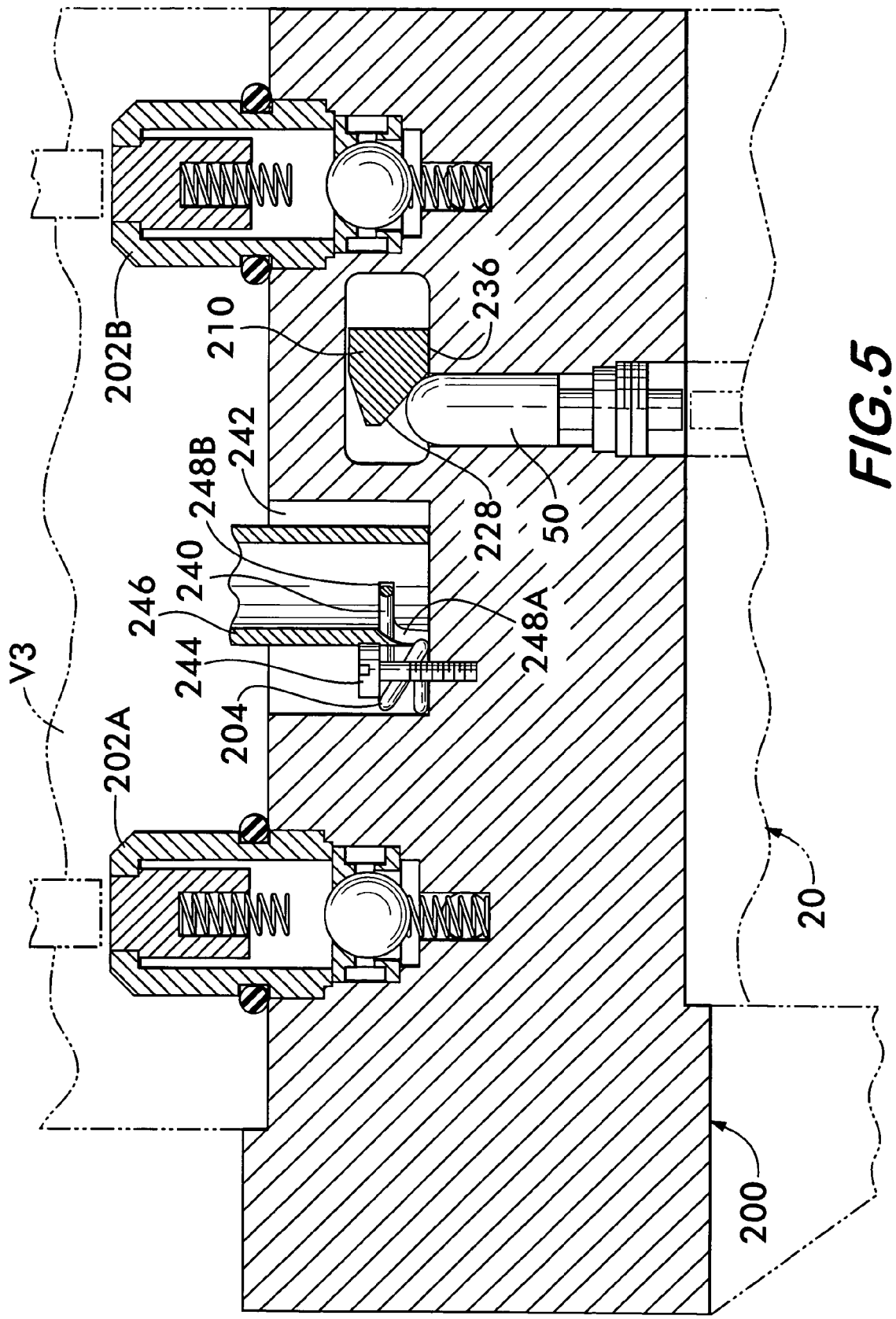
FIG. 5 is a sectional view taken along line 5-5 of FIG. 3.

The details of the construction and operation of the adaptor 200 will now be described. As best seen in FIGS. 3-5, the adaptor basically comprises a housing or block 202 having a pair of gas ports 202A and 202B, a first locking assembly 204, a motion translating assembly 208 and a second locking assembly 210. The ports 202A and 202B serve as the gas inlet and outlet ports coupling the carrier gas from the anesthesia machine to the vaporizer and from the vaporizer to the patient breathing circuit. As best seen in FIGS. 4 and 5 the ports 202A and 202B are of conventional construction. Moreover, the ports are mounted in the housing or block 202 in communication with various passageways and other components (unnumbered in those figures) to enable gas to flow through those components, passageways and ports in a conventional manner. Thus, in the interest of brevity the construction and operation of the ports, passageways and associated components, while shown in the drawings, will not be described herein. The locking assemblies 204 and 210, will however be described. later. Suffice it for now to state that the locking assembly 204 is constructed to releasably mount the vaporizer V3 on the adaptor 202 of the adaptor 200. The locking assembly 210 is constructed to releasably mount and lock the adaptor 200 on the bracket 30 of the interlock/exclusion system on the anesthesia machine.

The motion translating assembly 208 serves to couple the vertically upward/downward movement of the follower pin assembly 50 into a horizontally directed movement compatible with the movement of the extendable pins 28A and 28B of the vaporizer unit V3. The motion translating assembly basically comprises a pivotable lug 212, a pivot pin 214, a two-piece rod 216A and 216B, a pivotable link 218 and a pivot pin 220. The lug 212 is mounted within a recess or cavity 222 in the block 202 via the pivot pin 214. The recess or cavity 222 is located in the top surface of the block 202 adjacent one end thereof. The top surface 202 of the block is planar and includes an upwardly directed stop surface 224 adjacent the recess 222 (FIG. 4). The vaporizer unit V3 is adapted to be releasably mounted on the block with the housing of the vaporizer located on the top surface of the block and abutting the stop surface 224 as shown by the phantom lines in FIG. 4. The pivot pin 214 is disposed horizontally so that the lug 212 pivots about the horizontal axis defined by the pin. The upper end of the lug includes an arcuate side surface 212A which is arranged to engage the free end of the pin 28A of the vaporizer unit V3. The lower end of the lug includes an arcuate side surface 212B which is arranged to engage the free end of the rod 216A of motion translating assembly 208.

The rods 216A and 216B are elongated linear members located for longitudinal reciprocation within a horizontally extending bore in the block 202. One end of the bore is in communication with the cavity 222 so that the free end of the rod 216A can engage the lower arcuate surface 212B of the pivoting lug 212. Two rods 216A and 216B are used in place of a single rod (which could be used) to facilitate the assembly of the components of the adaptor 200. The rods 216A and 216B are aligned coaxially within the horizontal bore. The free end of the rod 216B is arranged to engage the pivotable link 210. The pivotable link 210 is mounted for pivoting action on the pivot pin 220. To that end a cavity 224 is provided in the block and is in communication with the bore in which the rod 216B is located so that the free end of that rod extends into the cavity. The pivot pin 220 has a threaded lower end which is screwed into a correspondingly threaded, vertically oriented bore in the block immediately below the cavity 224. The upper end of the pivot pin includes a slot to enable the pin to be screwed into place so that the pin extends vertically.

The pivotable link 210 is mounted on the pivot pin in the cavity 224 and includes a first end and a second end, with the pivot pin being located intermediate those ends. The first end of the pivotable link 210 has a ball or sphere 226 mounted therein which is arranged to engage the free end of the rod 216A. The second end of the pivotable link includes a downwardly extending sloped cam surface 228. This surface is arranged to engage the domed upper end of the follower pin assembly 50 as best seen in FIGS. 2A-2C, 3 and 5. The link 210 is adapted to be pivoted about the pin 220 in a horizontal plane. The link 210 is spring biased to ensure that the cam surface 228 is kept in engagement with the domed upper end of the follower pin assembly 50 and to tend to force the link in the direction of the arcuate arrow shown in FIG. 2A.

A helical compression spring 230 is located within a bore in the block 210. The bore is in communication with the cavity 228, so that the inner end of the spring 230 extends into the cavity and into engagement with the link. In particular, the link includes a recess 232 in its first end which receives the inner end of the spring 230. The spring is held in place under compression by a screw 234 located within the bore to apply a bias force on the pivotable link 210.

Figure 2A:
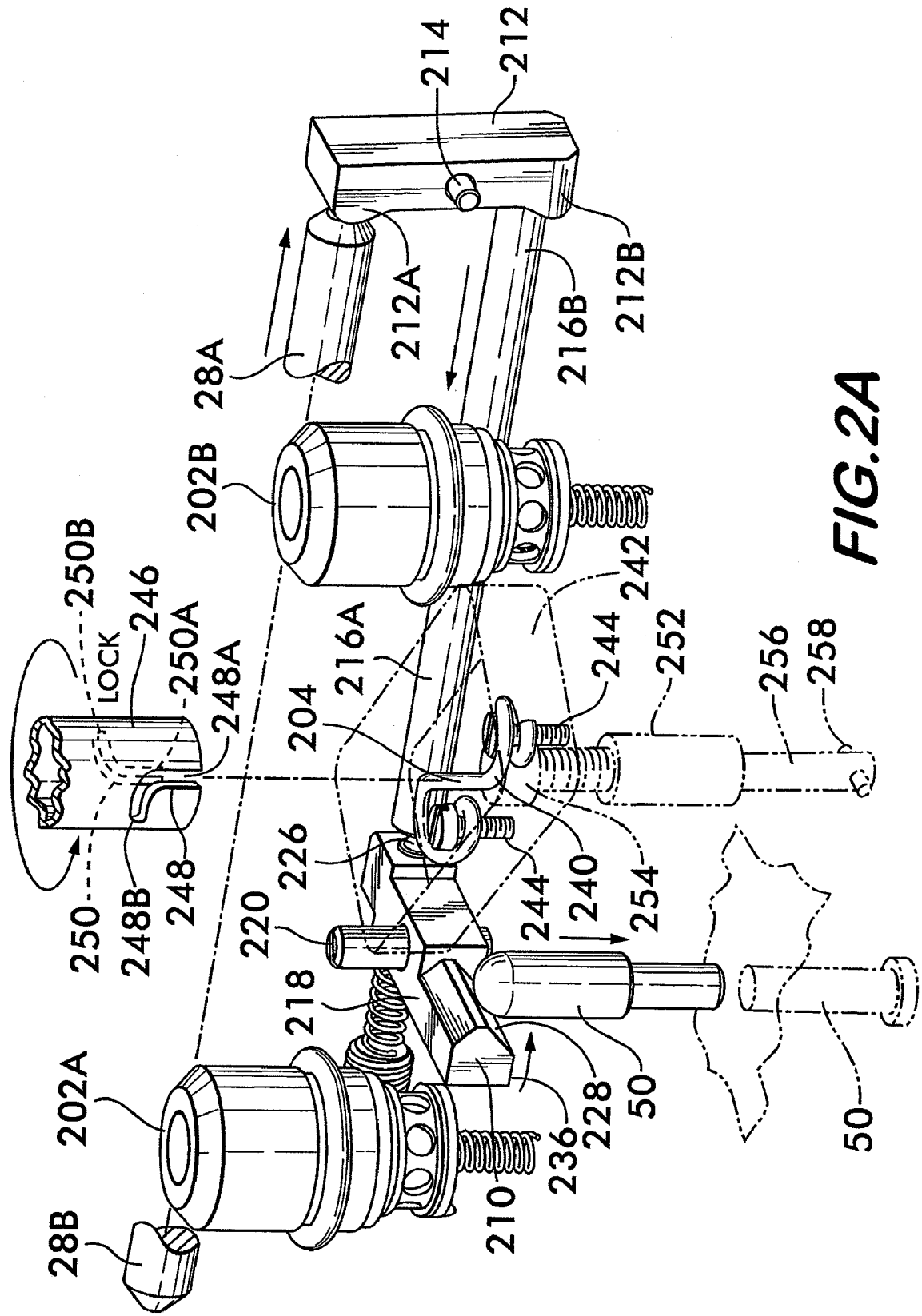
FIG. 2A is an enlarged isometric view of a portion of the adaptor of FIG. 1, and also showing a portion of the interlock the interlock/exclusion system in phantom lines, with the adaptor and interlock/exclusion system being shown in the condition wherein the vaporizer mounted on the adaptor is ready to be opened.
Figure 2B:
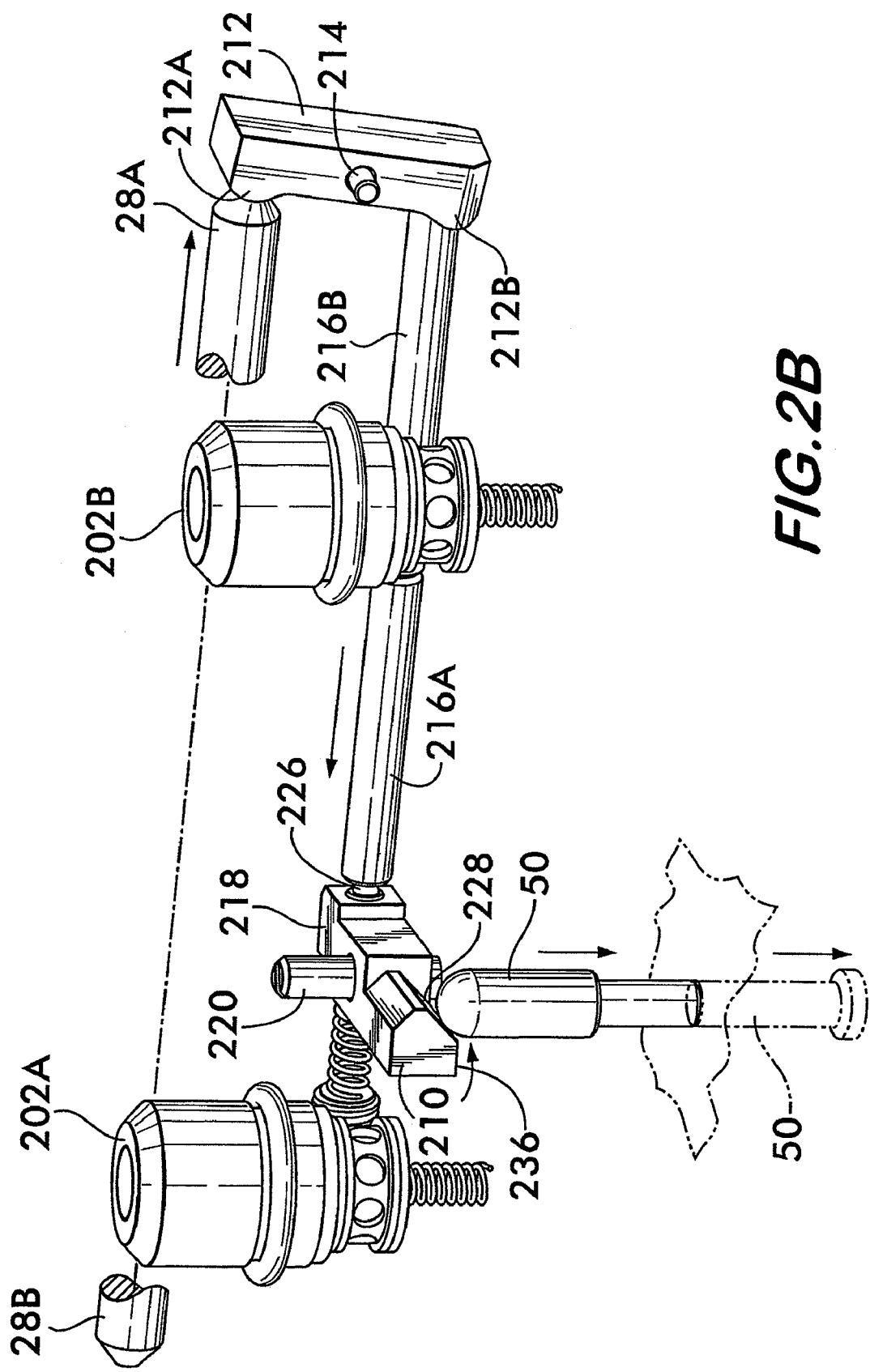
FIG. 2B is a view similar to FIG. 2A, but showing the adaptor and associated interlock/exclusion system during the opening of the vaporizer mounted on the adaptor.
Figure 2C:
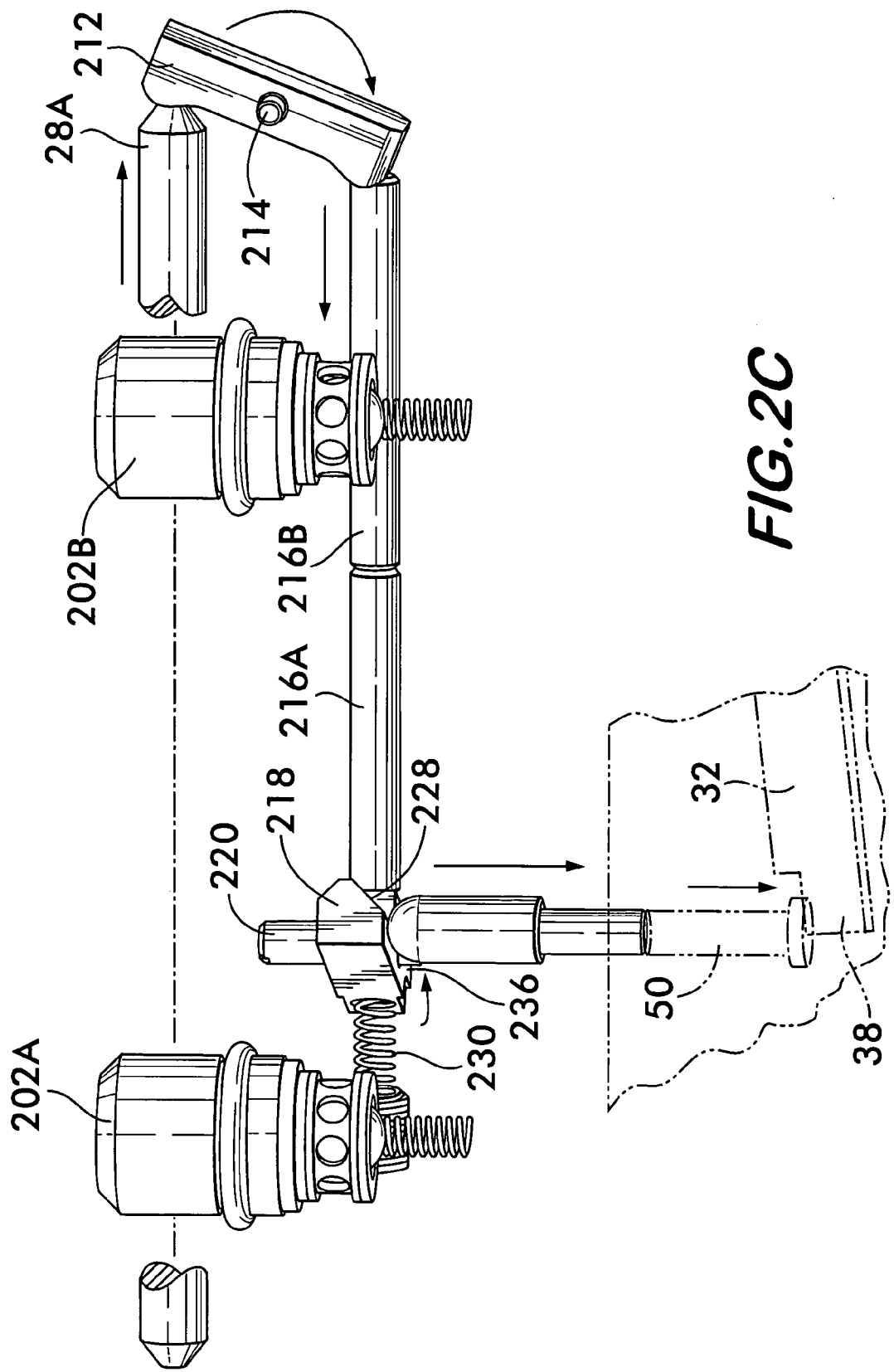
FIG. 2C is a view similar to FIGS. 2A and 2B, but showing the adaptor and associated interlock/exclusion system after the vaporizer mounted on the adaptor has been opened, whereupon the interlock/exclusion system prevents the opening of either of the other two vaporizers.

Operation of the motion translation assembly can best be understood by reference to FIGS. 2A-2C. To that end when the vaporizer unit V3 is opened, its pin 28A is extended horizontally outward, whereupon its free end engages the arcuate surface 212A of the lug 212. This action starts the lug to pivot in the clockwise direction, whereupon its lower arcuate surface 212B pushes on the free end of the rod 216B. Rod 216B pushes against rod 216A, whereupon the free end of rod 216A pushes against the ball 226 on the link 210 against the bias provided by the spring 230. This linear horizontal motion is translated by the link into an arcuate motion, i.e., the second end of the link starts to pivot about the pin 220 in the direction of the arcuate arrow in FIG. 2A. This arcuate or pivoting motion of the second end of the link is coupled by the cam surface 228 to the top portion of the follower pin assembly 50 thereby applying a downward force to that assembly in the direction of the arrow. The continued extension of the pin 28A from the housing of the vaporizer unit V3 effects the further pivoting of the lug 212, thereby pushing the pins 216A and 216B further to the left as seen in FIG. 2B, whereupon the link 210 is pivoted further in the direction of the arrow in that figure. This action causes the follower pin assembly 50 to move downward. When the vaporizer pin 28A has reached its fully extended position, the link 210 will have been pivoted to the position shown in FIG. 2C, whereupon the top surface of the upper end of the follower pin assembly 50 will reside on a flat horizontally oriented surface 236 of the link which is contiguous with the lower end of the cam surface 228. Rotation of the vaporizer adjustment dial to close the vaporizer V3, causes the pins 28A and 28B to be retracted. This action enables the spring 230 to pivot the link in the opposite direction from that described above, whereupon the rods 216A and 216B are enabled to slide to the right towards the lower end of the dog 212. The pivoting of the link 218 in that direction enables the top surface of the pin assembly 50 to ride off of the flat surface 236 and up the cam surface 228. This upward movement is coupled to the interlock/exclusion system in a manner similar to that described earlier.

The first locking assembly 204 which serves to releasably mount and lock the vaporizer unit V3 on the adaptor block 202 will now be described. That locking assembly is best seen in FIGS. 2A, 3 and 5 and basically comprises a generally S-shaped wire 240 mounted within a cavity 242 in the block 202 via a pair of mounting screws. The central portion of the wire 240 is generally linear and extends horizontally above the floor of the cavity 242. The linear central portion of the wire 240 is adapted to be releasably connected to a portion of the vaporizer unit V3. In particular, as seen in FIGS. 1 and 3, a downwardly projecting tube 246 having a diametrically opposed pair of slots 248 and 250 in its free end is coupled to the vaporizer unit V3. The slot 248 includes a longitudinally directed linear portion 248A extending parallel to the longitudinal axis of the tube 246 and a circumferentially directed portion 248B communicating with the slot portion 248A. In a similar manner the slot 250 includes a longitudinally directed linear portion 250A extending parallel to the longitudinal axis of the tube 246 and a circumferentially directed portion 250B communicating with the slot portion 250A.

When the vaporizer unit V3 is to be mounted on the adaptor block 202, the vaporizer unit is disposed on the block 202 and the slots of tube 246 are aligned with the linear central portion of the S-shaped wire 240 so that the linear portion of the wire 240 can be received in the slot portions 248A and 250A. The tube 246 is then pressed downward and rotated in the direction of the arrow shown in FIG. 2A to cause the central portion of the wire 240 to enter the slot portions 248A and 250A and from there to move into the circumferentially directed slot portions 248B and 250B, thereby releasably locking the vaporizer unit V3 to the adaptor 20.

The second locking assembly 210 which serves to releasably mount and lock the adaptor block 202 on the bracket 30 of the anesthesia machine will now be described. That assembly basically comprises an elongated cylindrical rod 252 having a threaded bore in its upper end in which a threaded screw 254 is located. The lower end 256 of the rod 252 is of smaller diameter and terminates in a transversely oriented locking pin 258. The rod 252 is disposed within a concomitantly shaped bore in the adaptor block 202 and is adapted to be rotated about its longitudinal axis by the insertion of a screw driver in the slotted head of the screw. The lower end portion 256 of the rod is adapted to be received within a vertically extending bore (not shown) in the bracket 30 of the interlock/exclusion system 20, so that when the rod is rotated the projecting locking pin engages an undersurface (not shown) of the bore in the bracket 30 to releasably mount the adaptor 200 thereto.

It should be pointed out at this juncture that the vaporizer unit V3 can be mounted on the bracket 30 of the interlock/exclusion system 20 at any of the three locations shown by means of the locking assembly 210 and respective bores in the interlock/exclusion system at the location of each of the other vaporizers units V1 and V2. Moreover, plural adaptors 200 of the subject invention can be used to mount plural vaporizer units, like vaporizer unit V3, at desired vaporizer receiving positions of the interlock/exclusion system whether or not any other vaporizer units are also mounted on thereon. Further still, as taught in my aforementioned patent application, the interlock exclusion system may include more than three vaporizer receiving locations, so that one or more adaptors of this invention can be used on anesthesia machines configured to mount more than three vaporizer units thereon.

While the invention has been described in detail and with reference to specific examples thereof, it will be apparent to one skilled in the art that various changes and modifications can be made therein without departing from the spirit and scope thereof.

What is claimed is:

1. An adaptor for use with an anesthesia machine having an interlock/exclusion system, the interlock/exclusion system being arranged to removably mount a first, second and third gas flow units thereon, each of the gas flow units being arranged to be opened to enable the anesthesia machine to provide a gas to a patient, one of said first, second and third gas flow units having a horizontally oriented pin arranged to move in a horizontally outward motion from that one gas flow unit when that one gas flow unit is opened, the interlock/exclusion system comprising vertically oriented pins associated with respective ones of the gas flow units, all of the vertically oriented pins being coupled to one another, whereupon when one of the gas flow units is opened the vertically oriented pin associated with it is moved downward and the vertically oriented pins of the other gas flow units are moved upward to preclude the opening of those other gas flow units, said adaptor being arranged to be mounted on the interlock/exclusion system and comprising means for coupling it to one of the vertically oriented pins of the interlock/exclusion system for releasably mounting the gas flow unit having the horizontally oriented pin on the anesthesia machine, the horizontally oriented pin being arranged to move in a horizontally outward motion when the gas flow unit is opened, said adaptor comprising an assembly of movable members connected between the horizontally oriented pin and an associated one of the vertically oriented pins to couple the horizontally outward motion of the horizontally oriented pin to the associated vertically oriented pin of the interlock/exclusion system to move the associated vertically oriented pin downward, whereupon the interlock/exclusion system operates to cause the other vertically oriented pins to extend upward and thereby prevent the opening of the other gas flow units mounted on the interlock/exclusion system.

2. The adaptor of claim 1, wherein said adaptor is arranged to be releasably mounted on the interlock/exclusion system.

3. The adaptor of claim 2 additionally comprising a first movable member and a second movable member, said first member being pivotable about a horizontal axis and having an upper end located adjacent the horizontally oriented pin of the gas flow unit having that pin, said second movable member being coupled to the first movable member and having a downward sloping cam face adapted to engage the associated vertically oriented pin to push the associated vertically oriented pin downward when the gas flow unit having the horizontally oriented pin is opened.

4. The adaptor of claim 3 wherein said first movable member has a lower end and wherein said adaptor additionally comprises at least one rod coupled between said lower end of said first movable member and said second movable member.

5. The adaptor of claim 4 wherein said second movable member is pivotable about a vertical axis and has a first end portion at which said cam surface is located and a second end portion, said second end portion being arranged to engage said at least one rod.

6. The adaptor of claim 5 additionally comprising a spring to bias said second end of said second movable member into engagement with said at least one rod.

7. The adaptor of claim 6 wherein the bias provided by said spring is adjustable.

8. The adaptor of claim 7 additionally comprising a first locking assembly for releasably locking the gas flow unit having the horizontally oriented pin on said adaptor.

9. The adaptor of claim 1 additionally comprising a first movable member and a second movable member, said first member being pivotable about a horizontal axis and having an upper end located adjacent the horizontally oriented pin of the gas flow unit having that pin, said second movable member being coupled to the first movable member and having a downward sloping cam face adapted to engage the associated vertically oriented pin to push the associated vertically oriented pin downward when the gas flow unit having the horizontally oriented pin is opened.

10. The adaptor of claim 9 wherein said first movable member has a lower end and wherein said adaptor additionally comprises at least one rod coupled between said lower end of said first movable member and said second movable member.

11. The adaptor of claim 10 wherein said second movable member is pivotable about a vertical axis and has a first end portion at which said cam surface is located and a second end portion, said second end portion being arranged to engage said at least one rod.

12. The adaptor of claim 11 additionally comprising a spring to bias the second end of the second movable member into engagement with said at least one rod.

13. The adaptor of claim 12 wherein the bias provided by said spring is adjustable.

14. The adaptor of claim 1 additionally comprising a first locking assembly for releasably locking the gas flow unit having the horizontally oriented pin on said adaptor.

* * * * *